United States Patent [19]

Manoury et al.

[11] Patent Number: 4,481,207

[45] Date of Patent: Nov. 6, 1984

[54] 1-PHENETHYL-ALPHA-PHENYL-PIPERIDINE-3-PROPANENITRILES AND THEIR PHARMACEUTICAL USES

[75] Inventors: Philippe Manoury, Le Plessis Robinson; Jean Binet, Breuillet; Gerard DeFosse, Paris, all of France

[73] Assignee: Synthelabo, Paris, France

[21] Appl. No.: 523,349

[22] Filed: Aug. 15, 1983

[30] Foreign Application Priority Data

Aug. 16, 1982 [FR] France ............... 82 14154

[51] Int. Cl.³ .................. A61K 31/445; C07D 211/34
[52] U.S. Cl. ................... 424/267; 546/197; 546/231
[58] Field of Search ............. 546/197, 231; 424/267

[56] References Cited

U.S. PATENT DOCUMENTS 4,399,286  8/1983  Lawson ................ 546/231

*Primary Examiner*—Robert T. Bond
*Attorney, Agent, or Firm*—Wegner & Bretschneider

[57] ABSTRACT

Compounds of the formula:

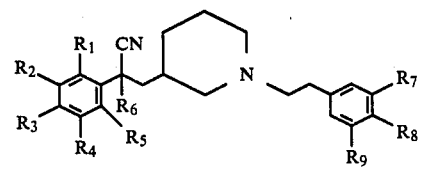

wherein $R_1$, $R_2$, $R_3$, $R_4$ and $R_5$ each represent a hydrogen atom, a halogen atom, a ($C_{1-4}$)alkoxy radical, a ($C_{1-4}$)alkylthio radical, a halogeno($C_{1-4}$)alkyl radical, a ($C_{1-4}$)alkyl radical or a cycloalkyl-alkoxy-alkoxy radical or two of the adjacent R symbols together form a methylenedioxy or ethylenedioxy radical, $R_6$ represents a hydrogen atom, a ($C_{1-4}$)alkyl radical, a ($C_{3-6}$)cycloalkyl radical or a ($C_{3-6}$)cycloalkyl-($C_{1-4}$)alkyl radical, and $R_7$, $R_8$ and $R_9$ each represent a hydrogen atom or a methoxy radical, are new compounds possessing pharmacological properties; they are useful as calcium antagonists and as antihypertensives.

9 Claims, No Drawings

1-PHENETHYL-ALPHA-PHENYL-PIPERIDINE-3-PROPANENITRILES AND THEIR PHARMACEUTICAL USES

DESCRIPTION

The present invention relates to new therapeutically useful 1-phenethyl-α-phenyl-piperidine-3-propanenitrile derivatives, to a process for their preparation and pharmaceutical compositions containing them.

The compounds of the present invention are those of the general formula:

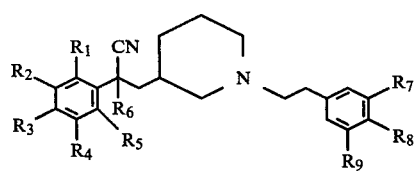

wherein $R_1$, $R_2$, $R_3$, $R_4$ and $R_5$ independently of one another each represent a hydrogen atom, a halogen atom, a ($C_{1-4}$)alkoxy radical, a ($C_{1-4}$)alkylthio radical, a halogeno($C_{1-4}$)alkyl radical, a ($C_{1-4}$)alkyl radical or a cycloalkylalkoxy-alkoxy radical, or two of the adjacent R symbols, viz $R_1$ and $R_2$, $R_2$ and $R_3$, $R_3$ and $R_4$ and $R_5$, together form a methylenedioxy or ethylenedioxy radical, $R_6$ represents a hydrogen atom, a($C_{1-4}$)alkyl radical, a ($C_{3-6}$)cycloalkyl radical or a ($C_{3-6}$)cycloalkyl-($C_{1-4}$)alkyl radical, and $R_7$, $R_8$ and $R_9$ independently of one another each represent a hydrogen atom or a methoxy radical, and pharmaceutically acceptable acid addition salts thereof.

It is to be understood that the alkyl and alkoxy radicals or moieties referred to in the definitions of symbols $R_1$–$R_6$ may have straight- or branched-chains.

The compounds of general formula (I) contain two asymmetric carbons and can consequently provide two pairs of diastereoisomers, which can be separated by fractional crystallisation of their salts or by chromatography.

The pair of diastereoisomers A denotes the product whose Rf value in thin layer chromatography is less than that of the pair of diastereoisomers B.

The oxalate of the pair of diastereoisomers A is more insoluble than that of the pair of diastereoisomers B. The NMR spectra of the pairs of diastereoisomers A and B are different and enable them to be identified.

The enantiomers of each pair of diastereoisomers are also part of the invention. They can be obtained either (i) by fractional crystallisation of salts with optically active acids, or (ii) by synthesis from a compound of general formula (III) depicted hereafter in which the relevant carbon atom of the piperidine nucleus has a known stereochemistry; this synthesis leads to two diastereoisomers of the RS and SS or RR and RS configuration, depending on the stereochemistry of the relevant carbon of the piperidine nucleus; these diastereoisomers can be separated by fractional crystallisation of their salts or by chromatography.

The preferred compounds of the invention are those of general formula (I) in which two of the symbols $R_1$ to $R_5$ are other than hydrogen atoms, and more particularly those in which the symbols $R_1$ to $R_5$ independently of one another each represent a methoxy, methylthio, methyl or 2-cyclopropylmethoxyethoxy radical or a hydrogen, chlorine or fluorine atoms, or two of the adjacent symbols $R_1$ to $R_5$ together represent a methylenedioxy or ethylenedioxy radical.

Amongst these compounds, those wherein $R_6$ represents an isopropyl, ethyl, cyclopentyl or cyclopropylmethyl radical or a hydrogen atom are preferred, and especially those wherein $R_6$ represents an isopropyl radical.

According to a feature of the invention, the compounds of general formula (I) are prepared according to the reaction depicted pictorially below:

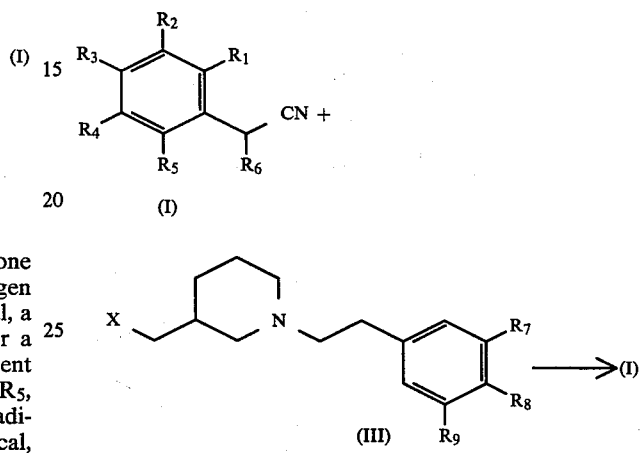

wherein X represents a labile group such as a halogen atom or an alkylsulphonyl or arylsulphonyl radical.

The reaction of the compound of general formula (II) with the compound of general formula (III) may be carried out (a) in toluene in the presence of sodium amide at a temperature of from 60° to 110° C., or (b) in a mixture of tetrahydrofuran and hexamethylphosphorotriamide (HMPT) in the presence of lithium diisopropylamide at a temperature of from −60° to +20° C., or (c) by phase transfer with an inorganic base such as sodium hydroxide, and a solvent such as toluene or methylene chloride, in the presence of a quaternary ammonium compound such as tetrabutylammonium chloride or bromide, at a temperature of from 20° to 100° C.

Some of the starting compounds of general formula (II) are new and some are described in the literature. They are prepared in accordance with methods described in the literature by reacting a compound of the general formula:

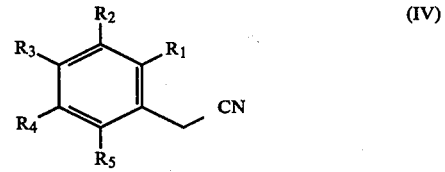

(wherein the symbols $R_1$–$R_5$ are as hereinbefore defined) with a compound $R_6Y$ (wherein Y represents a labile group such as X, and $R_6$ is as hereinbefore defined) in dimethyl sulphoxide in the presence of sodium hydroxide, or in dimethylformamide in the presence of sodium hydride, or in toluene in the presence of sodium amide.

The starting compounds of general formula (III) are new and can be prepared according to the following reaction schemes:

SCHEME 1

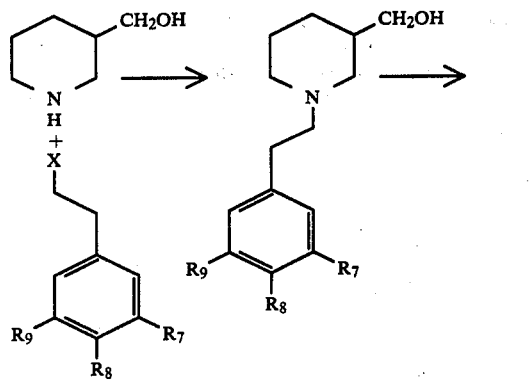

SCHEME 2

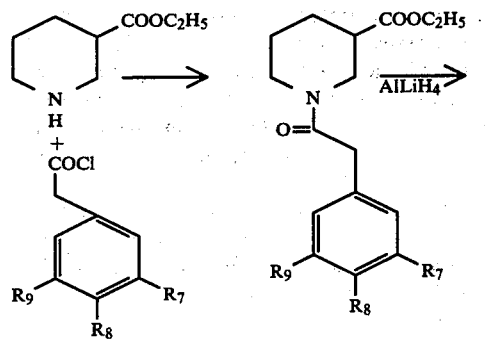

SCHEME 3

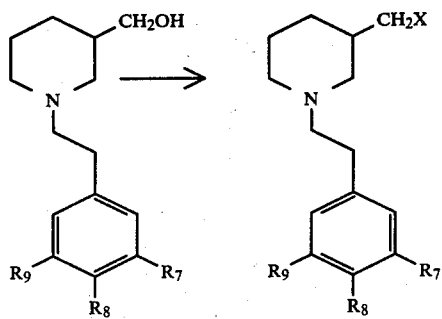

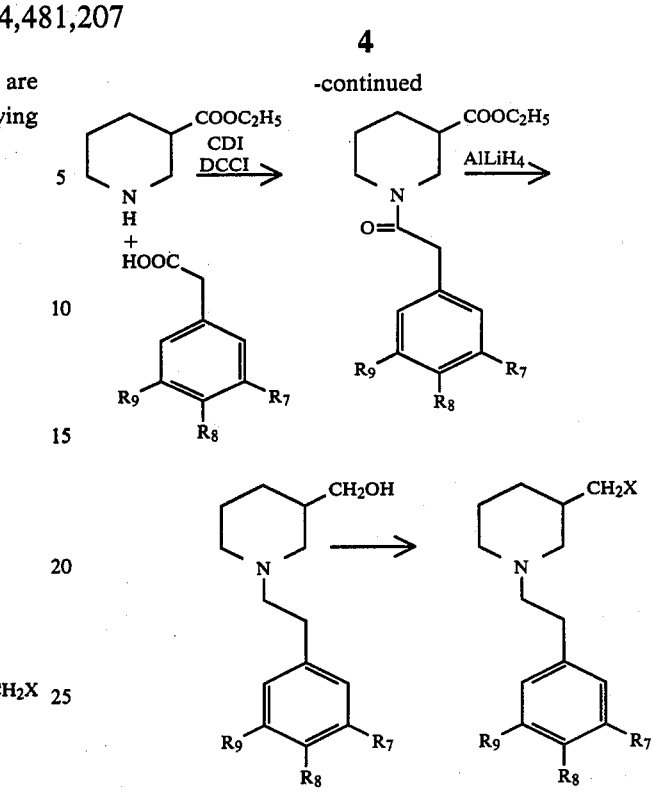

wherein the symbols $R_7$, $R_8$ and $R_9$ are as hereinbefore defined, and CDI is an abbreviation for carbonyldiimidazole and DCCI is an abbreviation for dicyclohexylcarbodiimide.

Pharmaceutically-acceptable acid addition salts of the compounds of general formula (I), e.g. methanesulphonates, mandelates, fumarates, oxalates, maleates, malonates, citrates, hydrochlorides, hydrobromides and hydroiodides, may be obtained by methods known per se, for example by treatment of the propionitrile base with the appropriate acid in a solvent medium, e.g. an alkanol or ether, or mixtures, thereof.

By the term 'methods known per se' as used in this specification is meant methods heretofore used or described in the literature.

The following Examples illustrate the preparation of compounds of general formula (I). The analyses and the IR and NMR spectra confirm the structures of the compounds.

EXAMPLE 1

α-(3,4-Dichlorophenyl)-1-[2-(3,4-dimethoxyphenyl)ethyl]-α-(1-methylethyl)-piperidine-3-propanenitride (a) 1-[(3,4-Dimethoxyphenyl)ethyl]-3-hydroxymethylpiperidine A mixture of 16 g (0.08 mol) of 3,4-dimethoxyphenylethyl chloride, 9.2 g (0.08 mol) of 3-hydroxymethylpiperidine, 2 g of sodium iodide, 17 g of sodium carbonate and 50 cc of methyl ethyl ketone is heated at the reflux temperature for one day. The solvent is then evaporated off and the residue is taken up in a mixture of dilute sodium hydroxide solution and diethyl ether. The ether phase is washed 3 times with water, dried over $Na_2SO_4$ and evaporated. After recrystallisation from diisopropyl ether, the 1-[3,4-dimethoxyphenyl)ethyl]-3-hydroxymethylpiperidine melts at 89° C.

The hydrochloride of this compound is prepared in acetone by reacting the base with a solution of hydrogen chloride in diethyl ether. It melts at 167° C.

(b) 1-[2-(3,4-Dimethoxyphenyl)ethyl]-3-chloromethylpiperidine

A mixture of 4.8 g (0.0152 mol) of the hydrochloride obtained under (a), 5.4 g (0.045 mol) of $SOCl_2$ and 50 cc of chloroform is stirred at ambient temperature for 2 hours. The mixture is then heated at the reflux temperature for 1 hour. The solvent is evaporated off in vacuo and the residue is taken up in toluene. After evaporation, the 1-[2-(3,4-dimethoxyphenyl)ethyl]-3-chloromethylpiperidine hydrochloride crystallises. After washing with acetone and diethyl ether, this compound melts at 171° C.

The base is obtained in the form of an oil by adding aqueous carbonate solution and diethyl ether.

(c) α-(3,4-Dichlorophenyl)-1-[2-(3,4-dimethoxyphenyl)ethyl]-α-(1-methylethyl)-piperidine-3-propanenitrile A mixture of 5 g (0.0219 mol) of 2-(3,4dichlorophenyl)-2-isopropylacetonitrile, 6 g (0.02 mol) of 1-[2-(3,4-dimethoxyphenyl)ethyl]-3-chloromethylpiperidine, a 50% suspension of 1.96 g (0.024 mol) of $NaNH_2$ in toluene and 40 cc of toluene is heated at a temperature of 70° C. for half an hour. The mixture is then heated gradually to the reflux temperature over 2 hours. The reaction mixture is cooled and extracted with diethyl ether and the ether extract is poured into iced water. After the usual treatments, the product is extracted with diethyl ehter, washed and dried. This gives an oily product, which is converted to the oxalate. This gives a precipitate which, after recrystallisation from methanol, gives the pair of diastereoisomers A in the form of the oxalate (melting point 208° C.), which is converted to the base and then to the hydrochloride (melting point 220° C.)

The other pair of diastereoisomers B is recovered from the filtrate by alkalinisation. This gives an oil, which is converted to the acid fumarate (melting point 176° C.) in an alcohol/diethyl ether mixture.

The base is freed and the hydrochloride is then prepared (melting point 201° C.)

EXAMPLE 2

1-[2-(3,4-Dimethoxyphenyl)ethyl]-α-(3,4-dimethoxyphenyl)-α-(1-methylethyl)-piperidine-3-propanenitrile A mixture of 3.5 g (0.0117 mol) of 1-[2-(3,4-dimethoxyphenyl)ethyl]-3-chloromethylpiperidine, 2.7 g (0.0123 mol) of 2-(3,4-dimethoxyphenyl)-2-isopropylacetonitrile, a 50% suspension of 1.09 g (0.014 mol) of $NaNH_2$ in toluene and 30 cc of toluene is heated at the reflux temperature for 8 hours. After 6 hours of refluxing, a further 0.1 g of the nitrile and 0.04 g of the 50% suspension of $NaNH_2$ are added.

After evaporation in vacuo and taking-up of the residue in a mixture of water and diethyl ether, the medium is dried and evaporated. The oil obtained is converted to the acid oxalate. Crystallisation gives one of the two pairs of diastereoisomers. After recrystallisation from methanol, the pair of diastereoisomers A in the form of the oxalate melts at 203° C. It is converted to the base and then to the more soluble fumarate which melts at 105° C.

The pair of diastereoisomers B in the form of the oxalate, obtained from the filtrate and then recrystallised, melts at 179° C.

EXAMPLE 3

1-[2-(3,4-Dimethoxyphenyl)ethyl]-α-(3,4,5-trimethoxyphenyl)-α-(1-methylethyl)-piperidine-3-propanenitrile A mixture of 5.3 g (0.0178 mol) of 1-[2-(3,4-dimethoxyphenyl)ethyl]-3-chloromethylpiperidine, 4.7 g (0.019 mol) of 2-(3,4,5-trimethoxyphenyl)-2-isopropylacetonitrile, a 50% suspension of 1.7 g (0.0212 mol) of $NaNH_2$ in toluene and 40 cc of toluene is heated at the reflux temperature, under nitrogen for 16 hours. During the reaction, an excess of nitrile is added and the equimolar amount of $NaNH_2$ until the starting chlorine compound has completely disappeared, reflux being continued.

After the usual washing and drying treatments, an oil is recovered, which is converted to the oxalate in ethanol.

The two pairs of diastereoisomers are separated by chromatography and converted to salts.

The pair of diastereoisomers A in the form of the acid fumarate melts at 146° C.

The pair of diastereoisomers B in the form of the hydrochloride melts at 192° C.

EXAMPLE 4

1-[2-(3,4-Dimethoxyphenyl)ethyl]-α-(2-methoxy-3,4-methylenedioxyphenyl)-α-(1-methylethyl)piperidine-3-propanenitrile (a) 2-(2-Methoxy-3,4-methylenedioxyphenyl)-2-isopropylacetonitrile The starting compound 2-(2-methoxy-3,4-methylenedioxyphenyl)-acetonitrile is described in the literature by A. Robertson and W. B. Whalley, J. Chem. Soc. 1440 (1954).

A solution of 6.5 g (0.034 mol) of this nitrile in 20 cc of dimethylformamide (DMF) is introduced into a suspension of 1.7 g (0.036 mol) of NaH (50% suspension in oil) in 100 cc of DMF.

When the addition has ended, 3.4 cc (0.036 mol) of 2-bromopropane are added and the mixture is stirred for half an hour at ambient temperature. The reaction mixture is then poured into 200 cc of iced water and extracted twice with diethyl ether. The ether phase is washed with water, dried and filtered and the filtrate is evaporated. The product is purified by column chromatography (eluant: $CH_2Cl_2$) and a pale yellow oil is collected.

(b) 1-[2-(3,4-Dimethoxyphenyl)ethyl]-3-chloromethylpiperidine is prepared in accordance with the process of Example 1.

(c) 1-[2-(3,4-Dimethoxyphenyl)ethyl]-α-(2-methoxy-3,4-methylenedioxyphenyl)-α-(1-methylethyl)-piperidine-3-propanenitrile A solution of 50 cc of tetrahydrofurane (THF) and 50 cc of HMPT containing 1.82 cc (0.025 mol) of diisopropylamine is cooled to −60° C. 10.6 cc (0.025 mol) of BuLi (1.6M in hexane) are added, under argon, at −60° C. The mixture is stirred for 15 minutes and a solution of 4.7 g (0.02 mol) of the nitrile prepared under (a) in 40 cc of THF is added. The mixture is stirred for half an hour, the temperature being allowed to rise to −40° C., and then cooled to −60° C. and a solution of 4.5 g (0.015 mol) of 1-[2-(3,4-dimethoxyphenyl)ethyl]-3-chloromethylpiperidine in 40 cc of THF is added. The mixture is allowed to return to ambient temperature and then left to stand for 48 hours. It is then poured into iced water and extracted twice with diethyl ether. The ether phase is washed with water, dried and filtered and the filtrate is evaporated.

The residual oil is chromatographed on a silica column.

The oxalate of the two pairs of diastereoisomers A and B is prepared in methanol. After recrystallisation from methanol, the oxalate of the pair of diastereoisomers A is obtained, which melts at 238° C.

The mother liquors from the crystallisation are evaporated. The residue is taken up in water, the mixture is rendered alkaline and extracted with $CH_2Cl_2$ and the extract is dried and evaporated. This gives the base in the form of an oil, which is converted to the hydrochloride in an ethyl acetate/diethyl ether mixture.

This product consists of the hydrochloride of the pair of diastereoisomers B, which melts at 210°–211° C.

EXAMPLE 5

1-[2-(3,5-Dimethoxyphenyl)ethyl]-α-(3,5-dimethoxyphenyl)-α-(1-methylethyl)-piperidine-3-propanenitrile (a) 2-(3,5-Dimethoxyphenyl)-2-isopropylacetonitrile This is prepared by reacting a solution of 2-(3,5-dimethoxyphenyl)-acetonitrile (4 g, 0.022 mol) in 10 cc of DMF with 2.86 g of isopropyl bromide in 5 cc of DMF, in the presence of a 50% suspension of 1.1 g of sodium hydride in 25 cc of DMF.

Boiling point (0.85 mm Hg) is 124° C.

(b) 1-[2-(3,5-Dimethoxyphenyl)ethyl]-3-chloromethylpiperidine 25 g of 2-(3,5-dimethoxyphenyl)-acetic acid in 100 cc of THF, 23 g of carbonyldiimidazole in 200 cc of THF and 20 g of ethyl piperidine-3-carboxylate are reacted at a temperature of 15° C.

A solution of the resulting ethyl 1-[(3,5-dimethoxyphenyl)-methylcarbonyl]-piperidine-3-carboxylate (38.5 g; 0.115 mol) in 100 cc of THF is reduced with a solution of 8 g of $AlLiH_4$ in 100 cc of THF.

This gives a pale yellow oil, which is converted to the hydrochloride.

A solution of the obtained 1-[2-(3,5-dimethoxyphenylethyl]-piperidine-3-methanol hydrochloride (8 g) in 50 cc of $CHCl_3$ is converted to 1-[2-(3,5-dimethoxyphenyl)ethyl]-3-chloromethylpiperidine with a solution of 6 cc of $SOCl_2$ in 10 cc of $CHCl_3$, under nitrogen.

(c) 1-[2-(3,5-Dimethoxyphenyl)ethyl]-α-(3,5-dimethoxyphenyl)-α-(1-methylethyl)-piperidine-3-propanenitrile A solution of 1.8 g (0.0175 mol) of diisopropylamine in 50 cc of THF and 50 cc of HMPT is cooled to −50° C. A solution of 11 cc (0.0175 mol) of 1.6M butyllithium is added dropwise.

The reaction mixture is stirred at −50° C. for 20 minutes, a solution of 2.75 g (0.0125 mol) of the nitrile prepared under (a) in 10 cc of THF is then added dropwise, the mixture is stirred again at −50° C. for 30 minutes and a solution of 3 g of the compound prepared under (b) in 10 cc of THF is then added. The reaction mixture is stirred for 1 hour at −50° C. and then left to stand overnight at ambient temperature. It is poured into 0.5 liter of a water/ice mixture, saturated with NaCl and extracted with diethyl ether. The organic phase is dried and evaporated. The oil obtained is chromatographed on a silica 60 column, elution being carried out with a 70/30 $CH_2Cl_2$/acetone mixture.

After evaporation of the solvents, the oil is dissolved in ethanol and a stoichiometric amount of oxalic acid is added. The pair of diastereoisomers A is filtered off and washed with ethanol and diethyl ether.

Melting point=210° C.

The mother liquors from the crystallisation are evaporated to dryness, the residue is then taken up in a $CH_2Cl_2$/$NaHCO_3$ mixture and the organic phase is left to separate out, dried and evaporated. The solution is chromatorgraphed and oxalic acid is added to give the oxalate of the pair of diastereoisomers B.

Melting point=150° C.

EXAMPLE 6

Enantiomers $A_1$, $A_2$, $B_1$ and $B_2$ of 1-[2-(3,4-dimethoxyphenyl)ethyl]-α-(3,4-dimethoxyphenyl)-α-(1-methylethyl)-piperidine-3-propanenitrile (a) Ethyl (R)(−)- and (S)(+)-piperidine-3-carboxylates A solution of 200 g (1.27 mol) of ethyl piperidine-3-carboxylate and 191 g (1.27 mol) of L(+)-tartaric acid in 800 cc of ethanol is left to stand for 4 days at 0°–5° C. The precipitate formed is filtered off and dried. After 2 recrystallisations from ethanol, 128 g of a product melting at 153° C. and having the (R) configuration are obtained.

$[\alpha]_D^{20} = +10.42°$ (c=5; $H_2O$).

The mother liquors are evaporated to dryness, the evaporation residue is taken up in a small amount of water, the mixture is rendered alkaline with a slight excess of concentrated sodium hydroxide solution and extraction is carried out twice with diethyl ether. The ether phase is dried with $MgSO_4$ and filtered and the filtrate is evaporated and distilled. This gives 73 g (0.46 mol) of an oil boiling at 103° C. under a vacuum of 7 mm of mercury. This oil is solubilised in 450 cc of ethanol containing 70 g (0.46 mol) of D(−)-tartaric acid. The solution is left to stand and, after filtration, 111 g of a salt are obtained which are recrystallized from 800 cc of ethanol containing 10 cc of water. The product having the (S) configuration melts at 154.5° C.

$[\alpha]_D^{20} = −10.1°$ (c=5; $H_2O$).

The tartrates are converted to the bases by alkalinisation with sodium hydroxide and extraction with diethyl ether.

This gives 59 g of ethyl (R)(−)-piperidine-3-carboxylate $[\alpha]_D^{20} = −1.9°$ (c=5; $H_2O$), and 45.6 g of ethyl (S)(+)-piperidine-3-carboxylate $[\alpha]_D^{20} = +2°$ (c=5; $H_2O$).

(b) 1-[2-(3,4-Dimethoxyphenyl)ethyl]-α-(3,4-dimethoxyphenyl)-α-(1-methylethyl)-piperidine(3,S)-3-propanenitrile (b) 1. (+)-3-Hydroxymethylpiperidine(3,R)

A solution of 20.1 g (0.128 mol) of ethyl (R)(−)-piperidine-3-carboxylate in 50 cc of diethyl ether is added dropwise to a suspension of 6.5 g (0.17 mol) of $AlLiH_4$ in 100 cc of dry diethyl ether in such a way that the ether is gently refluxing. After the addition has ended, the reflux is maintained for 1 hour. The mixture is then cooled and the complex is destroyed cautiously with a water/ethyl acetate mixture. The resulting mixture is filtered, the material on the filter is rinsed with diethyl ether and the filtrate is then evaporated. This gives 8.8 g (60%) of a crystalline product melting at 62° C. (boiling point=126° C. under 10 mm Hg).

$[\alpha]_D^{20} = +2.9°$ (c=0.6; pyridine).

(b) 2. (+)-1-[2-(3,4-Dimethoxyphenyl)ethyl]-3-hydroxymethylpiperidine(3,R)

A mixture of 8.6 g (0.075 mol) of (+)-3-hydroxymethylpiperidine(3,R), 16.5 g (0.082 mol) of 2-(3,4-dimethoxyphenyl)ethyl chloride, 3 g of NaI and 17 g (0.16 mol) of $Na_2CO_3$ in 50 cc of methyl ethyl ketone is heated at the reflux temperature for 60 hours. The reaction mixture is then evaporated, the residue is taken up in a water/diethyl ethyl mixture and the insoluble material is filtered off. The organic phase is washed with water, dried with $Na_2SO_4$ and filtered, and the filtrate is evaporated. The hydrochloride of the compound is prepared in an acetone/diethyl ether mixture. This gives a product melting at 188° C.

$[\alpha]_D^{20} = +8.4°$ (c=1 in $CH_3OH$).

(b) 3. (+)-1-[(3,4-Dimethoxyphenyl)ethyl]-3-chloromethylpiperidine(3,R)

12.5 cc (0.17 mol) of $SOCl_2$ in 60 cc of chloroform are added dropwise, with cooling at 5° C., to a solution of 18 g (0.057 mol) of (+)-1-[2-(3,4-dimethoxyphenyl)ethyl]-3-hydroxymethylpiperidine(3,R) hydrochloride in 200 cc of $CHCl_3$. The solution is allowed to return to ambient temperature over about 2 hours and is then heated at the reflux temperature for 1 hour 30 minutes. The mixture is cooled and evaporated. The evaporation residue is dissolved in 50 cc of methanol, 100 cc of diethyl ether are added and the mixture is left to crystallise slowly. This gives a product melting at 202° C.

$[\alpha]_D^{20} = +9.2°$ (c=1; $CH_3OH$).

(b) 4. 1-[2-(3,4-Dimethoxyphenyl)ethyl]-α-(3,4-dimethoxyphenyl)-α-(1-methylethyl)-piperidine(3,S)-3-propanenitrile A mixture of 12.1 g (0.04 mol) of 1-[2-(3,4-dimethoxyphenyl)ethyl]-3-chloromethylpiperidine(3,R), 10.1 g (0.046 mol) of α-(3,4-dimethoxyphenyl)-α-isopropylacetonitrile and 4.5 cc (0.057 mol) of sodium amide (as a 50% suspension in toluene) in 100 cc of toluene is heated at the reflux temperature for 12 hours, under nitrogen. The mixture is cooled, poured into water and extracted with diethyl ether. The extract is dried and filtered and the filtrate is evaporated. The residual oil is chromatographed on a silica column. This gives an oil.

The oxalate is prepared in ethyl acetate. This gives 5 g of product, which is taken up in 300 cc of boiling ethyl acetate. The boiling suspension is filtered and the insoluble material is recrystallised from ethanol. This gives the oxalate of enantiomer $A_1$, which melts at 172° C.

$[\alpha]_D^{20} = +82.2°$ (c=0.5; $CH_3OH$) for the base
$[\alpha]_D^{20} = +58°$ (c=1; $CH_3OH$) for the oxalate
(Rf=0.45, thin layer chromatography, Merck plate, eluant: AcOBu 47, AcOH 28, BuOH 8.5, $H_2O$ 16.5).

The filtrate is recovered and diethyl ether is added; by trituration and cooling, the oxalate of enantiomer $B_1$ is obtained, which melts at about 85° C.

$[\alpha]_D^{20} = +35.5°$ (c=1; $CH_3OH$).
(Rf=0.5, thin layer chromatography, Merck 5719 plate, eluant: AcoBu 47, AcOH 28, BuOH 8.5, $H_2O$ 16.5).

(c) 1-[2-(3,4-Dimethoxyphenyl)ethyl]-α-(3,4-dimethoxyphenyl)-α-(1-methylethyl)-piperidine(3,R)-3-propanenitrile (c) 1. Ethyl 1-[3,4-dimethoxyphenyl)-methylcarbonyl]-piperidine-3-carboxylate A suspension of 28.7 g (0.18 mol) of ethyl (S)(+)-piperidine-3-carboxylate in 200 cc of chloroform and 38.5 g of $Na_2CO_3$ is cooled to −20° C. A solution of 39.1 g (0.18 mol) of 3,4-dimethoxyphenylacetyl chloride in 100 cc of $CHCl_3$ is then added dropwise. The mixture is stirred for half an hour after the addition has ended, and the mixture is taken up in water and decanted. The organic phase is washed with water, dried and filtered and the filtrate is evaporated. This gives 48 g (79%) of an oil boiling at 210° C. under 0.02 mm Hg.

$[\alpha]_D^{20} = +43.3°$ (c=1; $CH_3OH$).

(c) 2. (−)-1-[2-(3,4-Dimethoxyphenyl)ethyl]-piperidine(3,S)-3-methanol

A solution of 45 g (0.134 mol) of ethyl (S)(+)-1-[(3,4-dimethoxyphenyl)-methylcarbonyl]-piperidine-3-carboxylate in 200 cc of THF is added dropwise to a suspension of 7.7 g (0.21 mol) of $AlLiH_4$ in 70 cc of THF. When the addition has ended, the mixture is heated at the reflux temperature for 1 hour 30 minutes. It is then cooled, the complex is hydrolysed and the mixture is then filtered. The precipitate is washed with THF and the filtrate is evaporated.

The hydrochloride is prepared in an ethanol/diethyl ether mixture. After recrystallisation from ethanol, this gives a product melting at 191° C.

$[\alpha]_D^{20} = -6.9°$ (c=1; $CH_3OH$).

(c) 3. 1-[2-(3,4-Dimethoxyphenyl)ethyl]-3-chloromethylpiperidine(3,S)

A solution of 22.2 g (0.07 mol) of (−)-1-[dimethoxyphenyl)ethyl]-piperidine(3,S)-3-methanol hydrochloride in 220 cc of $CHCl_3$ is cooled in an ice bath and 15.5 cc of thionyl chloride are added at this temperature. The mixture is allowed to return to ambient temperature over 1 hour 30 minutes and is then heated at the reflux temperature for 1 hour 30 minutes. The mixture is cooled and evaporated to dryness. The residue is taken up in methanol, and diethyl ether is added. The product crystallises. This gives a product melting at 203° C.

$[\alpha]_D^{20} = -9.5°$ (c=1; $CH_3OH$).

(c) 4. 1-[2-(3,4-Dimethoxyphenyl)ethyl]-α-(3,4-dimethoxyphenyl)-α-(1-methylethyl)-piperidine(3,R)-3-propanenitrile A mixture of 18 g (0.06 mol) of the compound obtained under (c)3, 16 g (0.07 mol) of α-(3,4-dimethoxyphenyl)-α-isopropylacetonitrile and 7 cc of $NaNH_2$ (as a 50% suspension in toluene) in 150 cc of toluene is heated at the reflux temperature for 10 hours. It is then cooled, taken up in water and extracted with diethyl ether. The organic phase is washed with water, dried with $Na_2SO_4$ and filtered and the filtrate is evaporated. After purification on a silica column, 17.6 g of an oil are obtained. The oxalate is prepared in ethyl acetate. After 2 recrystallisations from alcohol, the oxalate of enantiomer $A_2$ is obtained, which melts at 173° C.

$[\alpha]_D^{20} = -61.4°$ (c=1; $CH_3OH$) for the oxalate.
(Rf=0.45, thin layer chromatography, Merck Art 5719 plate, eluant: AcOBu 47, AcOH 28, BuOH 8.5, $H_2O$ 16.5)

$[\alpha]_D^{20} = -72°$ (c=0.5; $CH_3OH$) for the base.

The crystallisation filtrate is evaporated, the residue is taken up in water and the mixture is rendered alkaline and extracted with diethyl ether. The ether phase is washed with water, dried and filtered, and the filtrate is evaporated. The hydrochloride is prepared in an acetone/diethyl ether mixture. This gives the hydrochloride of enantiomer $B_2$, which melts at 165° C.

$[\alpha]_D^{20} = -36°$ (c=1; $CH_3OH$).
(Rf=0.5, thin layer chromatography, Merck Art 5719 plate, eluant: AcOBu 47, AcOH 28, BuOH 8.5, $H_2O$ 16.5).

EXAMPLE 7

Enantiomers A₂ and A₂ of
1-[2-(3,4-dimethoxyphenyl)ethyl]-α-(3,4-dimethoxyphenyl)-α-(1-methylethyl)-piperidine-3-propanenitrile
(by resolution of the pair of diastereoisomers)

A solution of 5 g (0.0167 mol) of 1-(3,4-dimethoxyphenylethyl)-3-chloromethylpiperidine in 4 cc of toluene is added to a suspension of 4 g (0.018 mol) of α-isopropyl-α-(3,4-dimethoxyphenyl)-acetonitrile, 8.7 g of powdered potassium hydroxide and 0.1 g of tetrabutylammonium bromide in 4 cc of toluene. The mixture is heated at 50° C. for 6 hours. It is then cooled, poured into iced water and extracted with diethyl ether. The organic phase is washed with water, dried with Na₂SO₄ and filtered and the filtrate is evaporated.

The oxalate is prepared in methanol. After recrystallisation from methanol, 2.1 g of the oxalate of the pair of diastereoisomers A, which melts at 203° C., are obtained (the fumarate prepared in an acetone/diethyl ether mixture melts at 105° C.). 1 g of the pair of diastereoisomers in the form of the base and 0.8 g of (−)-dibenzoyltartaric acid are solubilised in 10 cc of ethyl acetate. The solution is left to stand for 12 hours and the crystals obtained are then filtered off.

After 2 recrystallisations from ethyl acetate, the (−)-dibenzoyltartrate of enantiomer A₂ is obtained, which melts at 135° C.

$[\alpha]_D^{20} = -86.2°$ (c=1; CH₃OH).
$[\alpha]_D^{20} = -77°$ (c=0.5; CH₃OH) for the base.

The filtrate from the crystallisation is evaporated; after the usual treatment for regenerating the base, it is solubilised in 7 cc of ethyl acetate and 0.55 g of (+)-dibenzoyltartaric acid and the mixture is left to crystallise. After recrystallisation from ethyl acetate, the (+)-dibenzoyltartrate of enantiomer A₁ is obtained, which melts at 138° C.

$[\alpha]_D^{20} = +89.4°$ (c=1; CH₃OH)
$[\alpha]_D^{20} = +78°$ (c=0.5; CH₃OH) for the base.

The scheme for the synthesis, described in Example 6, of enantiomers A₁, A₂, B₁ and B₂ is given on the following pages.

Synthesis of the enantiomers of compounds 1 and 2

1st part

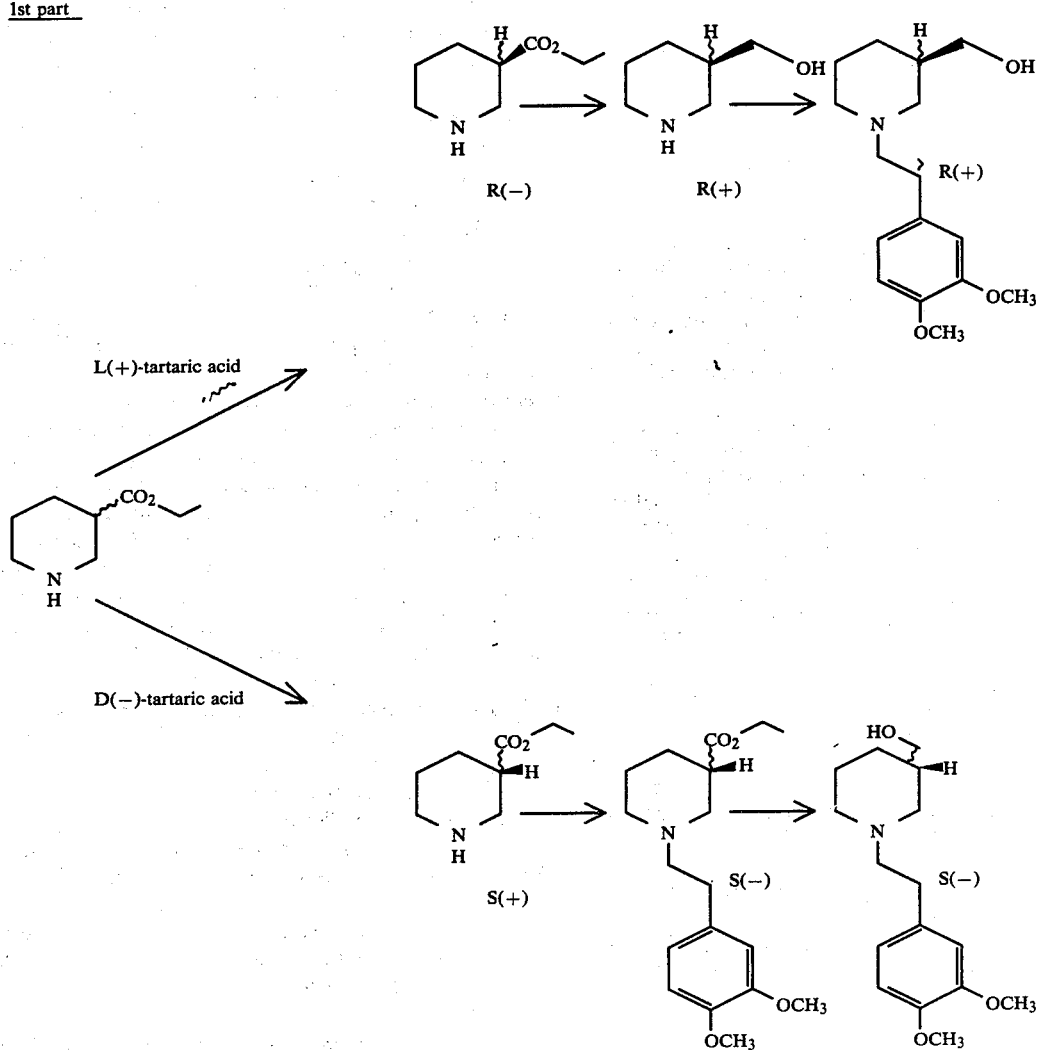

2nd part

-continued
Synthesis of the enantiomers of compounds 1 and 2

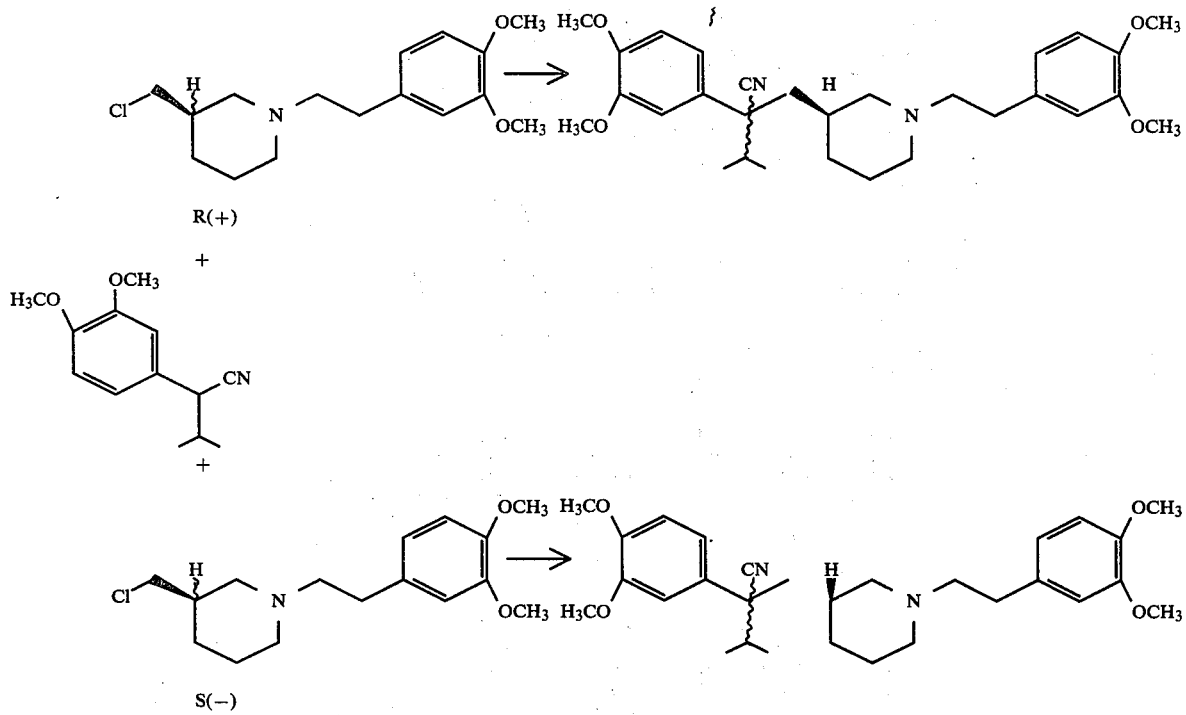

R(+)

+

S(−)

The compounds of the invention which were prepared by way of examples are shown in the Table which follows.

TABLE

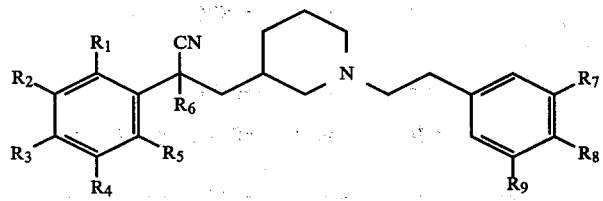

| Compound | $R_1$ | $R_2$ | $R_3$ | $R_4$ | $R_5$ | $R_6$ | $R_7$ | $R_8$ | $R_9$ | Salt | M.p. | Diastereoisomer |
|---|---|---|---|---|---|---|---|---|---|---|---|---|
| 1 | —H | —OCH$_3$ | —OCH$_3$ | —H | —H | —isopr | —OCH$_3$ | —OCH$_3$ | —H | oxalate | 179° | B |
| 2 | —H | —OCH$_3$ | —OCH$_3$ | —H | —H | —isopr | —OCH$_3$ | —OCH$_3$ | —H | fumarate | 105° | A |
| 3 | —H | —OCH$_3$ | —OCH$_3$ | —OCH$_3$ | —H | —isopr | —OCH$_3$ | —OCH$_3$ | —H | hydrochl. | 192° | B |
| 4 | —H | —OCH$_3$ | —OCH$_3$ | —OCH$_3$ | —H | —isopr | —OCH$_3$ | —OCH$_3$ | —H | fumarate | 146° | A |
| 5 | —H | —Cl | —OCH$_3$ | —H | —H | —isopr | —OCH$_3$ | —OCH$_3$ | —H | hydrochl. | 220° | A |
| 6 | —H | —Cl | —Cl | —H | —H | —isopr | —OCH$_3$ | —OCH$_3$ | —H | hydrochl. | 201° | B |
| 7 | —OCH$_3$ | —OCH$_3$ | —OCH$_3$ | —H | —H | —isopr | —OCH$_3$ | —OCH$_3$ | —H | oxalate | 200° | A |
| 8 | —OCH$_3$ | —OCH$_3$ | —OCH$_3$ | —H | —H | —isopr | —OCH$_3$ | —OCH$_3$ | —H | hydrochl. | 184° | B |
| 9 | —H | —OCH$_3$ | —OCH$_3$ | —H | —H | —H | —OCH$_3$ | —OCH$_3$ | —H | oxalate | 142° | |
| 10 | —H | —OCH$_3$ | —OCH$_3$ | —H | —H | —Et | —OCH$_3$ | —OCH$_3$ | —H | oxalate | 170° | A |
| 11 | —H | —OCH$_3$ | —OCH$_3$ | —H | —H | —Et | —OCH$_3$ | —OCH$_3$ | —H | oxalate | 158° | B |
| 12 | —H | —OCH$_3$ | —OCH$_3$ | —H | —H | cyclopentyl | —OCH$_3$ | —OCH$_3$ | —H | oxalate | 179/180° | A |
| 13 | —H | —OCH$_3$ | —OCH$_3$ | —H | —H | " | —OCH$_3$ | —OCH$_3$ | —H | oxalate | 190/191° | B |
| 14 | —H | —OCH$_3$ | —OCH$_3$ | —H | —H | cyclopropyl | —OCH$_3$ | —OCH$_3$ | —H | hydrochl. | 188° | B |
| 15 | —H | —OCH$_3$ | —OCH$_3$ | —H | —H | " | —OCH$_3$ | —OCH$_3$ | —H | oxalate | 175° | A |
| 16 | —H | —OCH$_3$ | —S—CH$_3$ | —OCH$_3$ | —H | —isopr | —OCH$_3$ | —OCH$_3$ | —H | hydrochl. | 178° | mix- |

TABLE -continued

| Compound | R₁ | R₂ | R₃ | R₄ | R₅ | R₆ | R₇ | R₈ | R₉ | Salt | M.p. | Diastereoisomer |
|---|---|---|---|---|---|---|---|---|---|---|---|---|
| 17 | —H | —Cl | —OCH₃ | —H | —H | —isopr | —OCH₃ | —OCH₃ | —H | fumarate | 155° | B |
| 18 | —H | —Cl | —OCH₃ | —H | —H | —isopr | —OCH₃ | —OCH₃ | —H | fumarate | 184° | A |
| 19 | —H | —OCH₃ | —H | —OCH₃ | —H | —isopr | —OCH₃ | —OCH₃ | —H | oxalate | 204° | A |
| 20 | —H | —OCH₃ | —H | —OCH₃ | —H | —isopr | —OCH₃ | —OCH₃ | —H | fumarate | 70° | B |
| 21 | —Cl | —Cl | —OCH₃ | —H | —H | —isopr | —OCH₃ | —OCH₃ | —H | hydrochl. | 153/154° | A |
| 22 | —Cl | —Cl | —OCH₃ | —H | —H | —isopr | —OCH₃ | —OCH₃ | —H | fumarate | 220/221° | B |
| 23 | —H | —OCH₃ | —OCH₃ | —H | —H | —isopr | —OCH₃ | —OCH₃ | —H | oxalate | ≈85° | B₁ |
| 24 | —H | —OCH₃ | —OCH₃ | —H | —H | —isopr | —OCH₃ | —OCH₃ | —H | oxalate | 172° | A₁ |
| 25 | —H | —OCH₃ | —OCH₃ | —H | —H | —isopr | —OCH₃ | —OCH₃ | —H | hydrochl. | 165° | B₂ |
| 26 | —H | —OCH₃ | —OCH₃ | —H | —H | —isopr | —OCH₃ | —OCH₃ | —H | oxalate | 173° | A₂ |
| 27 | —H | —OCH₃ | —O–CH₂–O— (R₃–R₄) | | —H | —isopr | —OCH₃ | —OCH₃ | —H | hydrochl. | 178/179° | B |
| 28 | —H | —OCH₃ | " | | —H | —isopr | —OCH₃ | —OCH₃ | —H | hydrochl. | 247° | A |
| 29 | —H | —OCH₃ | —CH₃ | —OCH₃ | —H | —isopr | —OCH₃ | —OCH₃ | —H | hydrochl. | 207° | B |
| 30 | —H | —OCH₃ | —CH₃ | —OCH₃ | —H | —isopr | —OCH₃ | —OCH₃ | —H | fumarate | 150° | A |
| 31 | —H | —OCH₃ | —Cl | —H | —H | —isopr | —OCH₃ | —OCH₃ | —H | hydrochl. | 115/116° | B |
| 32 | —H | —OCH₃ | —Cl | —H | —H | —isopr | —OCH₃ | —OCH₃ | —H | oxalate | 227/228° | A |
| 33 | —H | —OCH₃ | —Cl | —OCH₃ | —H | —isopr | —OCH₃ | —OCH₃ | —H | fumarate | 158° | A |
| 34 | —H | —OCH₃ | —Cl | —OCH₃ | —H | —isopr | —OCH₃ | —OCH₃ | —H | fumarate | 145° | B |
| 35 | —H | —OCH₃ | —H | —H | —H | —isopr | —OCH₃ | —OCH₃ | —H | oxalate | 166° | B |
| 36 | —H | —OCH₃ | —H | —H | —H | —isopr | —OCH₃ | —OCH₃ | —H | oxalate | 206° | A |
| 37 | —H | —OCH₃ | —OCH₃ | —H | —H | —isopr | —OCH₃ | —H | —H | oxalate | 178° | A |
| 38 | —H | —OCH₃ | —O–CH₂CH₂–O— (R₃–R₄) | | —H | —isopr | —OCH₃ | —OCH₃ | —H | hydrochl. | 186/188° | B |
| 39 | —H | —OCH₃ | " | | —H | —isopr | —OCH₃ | —OCH₃ | —H | oxalate | 222° | A |
| 40 | —OCH₃ | —O–CH₂–O— (R₂–R₃) | | —H | —H | —isopr | —OCH₃ | —OCH₃ | —H | oxalate | 238° | A |
| 41 | —OCH₃ | " | | —H | —H | —isopr | —OCH₃ | —OCH₃ | —H | hydrochl. | 210/211° | B |
| 42 | —H | —H | —O–CH₂–O— (R₃–R₄) | | —H | —isopr | —OCH₃ | —OCH₃ | —H | hydrochl. | 215/220° | A |
| 43 | —H | —H | " | | —H | —isopr | —OCH₃ | —OCH₃ | —H | hydrochl. | 172/173° | B |
| 44 | —H | —OCH₃ | —H | —H | —H | —isopr | —OCH₃ | —H | —H | oxalate | 178° | A |
| 45 | —H | —OCH₃ | —H | —H | —H | —isopr | —OCH₃ | —H | —H | oxalate | 145° | B |
| 46 | —Cl | —OCH₃ | —OCH₃ | —H | —H | —isopr | —OCH₃ | —OCH₃ | —H | oxalate | 197° | A |
| 47 | —H | —OCH₃ | —OCH₃ | —H | —H | —isopr | —OCH₃ | —H | —H | oxalate | 132° | B |
| 48 | —H | —OCH₃ | —OCH₃ | —H | —H | —isopr | —OCH₃ | —OCH₃ | —H | oxalate | 157/158° | B |
| 49 | —H | —OCH₃ | —H | —OCH₃ | —H | —isopr | —OCH₃ | —H | —OCH₃ | oxalate | 210° | A |
| 50 | —H | —OCH₃ | —H | —OCH₃ | —H | —isopr | —OCH₃ | —H | —OCH₃ | oxalate | 150° | B |
| 51 | —H | —OCH₃ | —OCH₃ | —H | —H | —isopr | —OCH₃ | —H | —OCH₃ | oxalate | 202° | A |
| 52 | —O–CH₂–O— (R₁–R₂) | | —OCH₃ | —H | —H | —isopr | —OCH₃ | —OCH₃ | —H | fumarate | 179/180° | A |
| 53 | —H | —OCH₃ | CME[a] | —H | —H | —isopr | —OCH₃ | —OCH₃ | —H | oxalate | 184° | A |
| 54 | —H | —OCH₃ | " | —H | —H | —isopr | —OCH₃ | —OCH₃ | —H | oxalate | 72/74° | B |
| 55 | —H | —H | F | —H | —H | —isopr | —OCH₃ | —OCH₃ | —H | oxalate | 172/174° | mixture |
| 56 | —OCH₃ | —OCH₃ | —O–CH₂–O— (R₃–R₄) | | —H | —isopr | —H | —OCH₃ | —OCH₃ | oxalate | 192° | A |
| 57 | —OCH₃ | —OCH₃ | " | | —H | —isopr | —H | —OCH₃ | —OCH₃ | oxalate | 154° | B |
| 58 | —H | —OCH₃ | " | | —OCH₃ | —isopr | —H | —OCH₃ | —OCH₃ | oxalate | 209/210° | A |
| 59 | —H | —OCH₃ | " | | —OCH₃ | —isopr | —H | —OCH₃ | —OCH₃ | oxalate | 148/150° | B |

[a]CME = cyclopropylmethoxyethoxy

The compounds of the invention were subjected to pharmacological tests which revealed their activity as calcium antagonists and as antihypertensives.

The experimental procedure used is a variant of that used by Godfraind and Kaba (1969) (blockage or reversal of the contraction induced by calcium and adrenaline in depolarised arterial smooth muscle. Br. J. Pharmac., 36, 549–560).

The experiments were carried out on sections of a rabbit's thoracic aorta. The animals, "Fauves de Bourgogne" (large fawn-coloured rabbits with white spots) weighing an average of 1.5 kg, are sacrificed by dislocation of the cervix and exsanguination. The thoracic aorta is rapidly removed and placed in an oxygenated bicarbonated Krebs medium (95% $O_2$+5% $CO_2$).

Aorta sections of about 1 cm in length are prepared and placed in 20 ml organ dishes containing oxygenated bicarbonated Krebs solution (pH 7.4) at 37° C. Two "U"-shaped metal hooks of the same length as the sections are introduced into the lumen in the latter. One of the hooks is fixed to the base of the dish. The other, which is connected to an isometric stress gauge (Grass FT03), makes it possible to record the contractile responses of the aorta sections on a pen oscillograph (Grass 79B) via a direct-current preamplifier (Grass 7P1). Compared with the spiral or ring preparations this method has the advantage of having more regard for the structural integrity of the vessels and of only recording the radial component of the contractile responses, which represents the interesting phenomenon from the functional point of view (regulation of the arterial pressure). An initial tension of 4 g is applied to the preparations.

Phenoxybenzamine (1 μM) and propanolol (1 μM) are added to the various Krebs media in order to suppress the contractile responses associated with the activation of the vascular α- and β-adrenergic receptors.

After stabilisation for one hour in the bicarbonated Krebs medium, the tension applied to the aortas is reduced to 2 g. After a waiting period of 30 minutes, the preparations are incubated for about ten minutes in a calcium-free bicarbonated Krebs solution in the presence of EDTA (200 μM) and propanolol (1 μM). This solution is then replaced by a calcium-free depolarising Krebs medium (rich in potassium) containing propanolol (1 μM). After 5 minutes, a single concentration of 1 mM of calcium is added to this solution and a stabilisation period of 30 minutes is observed, which enables the preparations to reach a stable contraction.

Then, cumulative doses of the compounds to be tested are administered every 30 minutes (the time generally necessary to obtain a plateau) until the contraction caused by the concentration of 1 mM of calcium has totally disappeared, or alternatively until the maximum concentration of 30 μM of product has been reached. At the end of the experiment, a supramaximum concentration of papaverin (300 μM) is administered in order to determine the maximum possible decontraction of each preparation.

The absolute values (in grams) of the initial contraction (after 1 mM of $CaCl_2$) and of the contraction after the various cumulative concentrations of vasodilating compounds are obtained, for each preparation, by subtraction of the minimum contraction observed 30 minutes after the final addition of a concentration of 300 μM of papaverin. The percentage decrease in the contraction, relative to the contraction caused by a concentration of 1 mM of calcium, is calculated for each dose of compound and each preparation, and this individual percentage decontraction is averaged: $\overline{X}$+S.E.M. The average values obtained (weighted by the reciprocal of the standard error in the mean) are analysed with the aid of a mathematical sigmoid-curve model, and the molar concentration causing 50% decontraction of the calcium response ($EC_{50}$) is calculated.

For the compounds of the invention, the $EC_{50}$ (μM) varies from 0.5 to 1.

The antihypertensive activity of the compounds of the invention was determined in accordance with the method of Gerald and Tschirky (Arzneim. Forsch. 1968, 18, 1285). The systolic pressure is measured by taking the pulse in the region of the caudal artery. The reduction in the pressure is about 30 to 40% after 2 hours and after 4 hours at a dose of 50 mg/kg, administered orally.

The compounds of the invention can be used for the treatment of all diseases for which calcium antagonists can be used, such as chest angina, dysrythmia or supraventricular origin, hypertension, cardiomyopathy, myocardial protection for patients who are at risk of infarctus or have suffered an infarctus, cardiac arrest, cerebrovascular diseases, mania and migraines. They can also be used as antihypertensive medicaments in the cardiovascular field. They are used in the treatment of all forms of essential or secondary hypertension.

The compounds of the invention can be presented in any form suitably for oral or parenteral administration, in association with any suitable excipient, for example in the form of tablets, gelatine capsules, ordinary capsules, and solutions to be taken orally or injected.

The daily dosage can range from 10 to 500 mg, administered orally, and from 3 to 50 mg, administered parenterally.

We claim:

1. 1-Phenethyl-α-phenyl-piperidine-3-propanenitriles, in the form of two pairs of diastereoisomers and/or in the form of enantiomers, corresponding to the general formula:

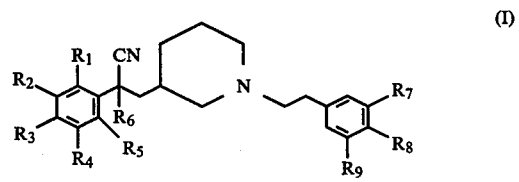

(I)

wherein $R_1$, $R_2$, $R_3$, $R_4$ and $R_5$ independently of one another each represent a hydrogen atom, a halogen atom, a ($C_{1-4}$)alkoxy radical, a ($C_{1-4}$)alkylthio radical, a halogeno($C_{1-4}$)alkyl radical, a ($C_{1-4}$)alkyl radical or a cycloalkyl-alkoxy-alkoxy radical or two of the adjacent R symbols together form a methylenedioxy or ethylenedioxy radical, $R_6$ represents a hydrogen atom, a ($C_{1-4}$)alkyl radical, a ($C_{3-6}$)cycloalkyl radical or a ($C_{3-6}$)cycloalkyl($C_{1-4}$)alkyl radical, and $R_7$, $R_8$ and $R_9$ independently of one another each represent a hydrogen atom or a methoxy radical, and pharmaceutically acceptable acid addition salts thereof.

2. A compound according to claim 1 wherein two of the symbols $R_1$ to $R_5$ represent atoms or radicals other than hydrogen.

3. A compound according to claim 2 wherein the symbols $R_1$ to $R_5$ independently of one another each represent a methoxy, methylthio, methyl or 2-cyclopropylmethoxyethoxy radical or a hydrogen, chlorine or fluorine atom, or two of the adjacent symbols $R_1$ to $R_5$ together represent a methylenedioxy or ethylenedioxy radical.

4. A compound according to claim 1, wherein $R_6$ represents an isopropyl, ethyl, cyclopentyl or cyclopropylmethyl radical or a hydrogen atom.

5. A compound according to claim 1 wherein $R_6$ represents the isopropyl radical.

6. A compound according to claim 1 wherein two of the symbols $R_1$ to $R_5$ represent a methoxy radical or two of the adjacent symbols $R_1$ to $R_5$ represent the methylenedioxy or ethylenedioxy radical and another of the symbols $R_1$ to $R_5$ represents a hydrogen atom or the methoxy radical, $R_6$ represents the isopropyl radical, $R_7$ and $R_8$ each represent a methoxy radical and $R_9$ represents a hydrogen atom.

7. A pharmaceutical composition comprising as active ingredient an effective amount of at least one propane-nitrile as claimed in claim 1 or a pharmaceutically acceptable acid addition salt thereof, in association with a pharmacologically-acceptable carrier.

8. A method for the treatment of a patient with an ailment for which a calcium antagonist can be used which comprises administering to the patient an amount of a compound as claimed in claim 1, or a pharmaceutically-acceptable acid addition salt thereof, sufficient to ameliorate the condition of the patient.

9. A method for the treatment of a patient requiring an antihypertensive medicament which comprises administering to the patient an amount of a compound as claimed in claim 1, or a pharmaceutically-acceptable acid addition salt thereof, sufficient to ameliorate the condition of the patient.

* * * * *